United States Patent [19]

Paris

[11] Patent Number: 4,857,519

[45] Date of Patent: Aug. 15, 1989

[54] NOVEL PHARMACEUTICAL COMPOSITIONS ENDOWED WITH ANTI-PROGESTERONIC PROPERTIES AND A PROCESS FOR MAKING THE SAME

[76] Inventor: Jacques Paris, 31 Cap de Croix, 06100 Nice, France

[21] Appl. No.: 46,936

[22] Filed: May 5, 1987

[30] Foreign Application Priority Data

May 5, 1986 [FR] France .................................. 86 06457

[51] Int. Cl.$^4$ ............................................. A61K 31/56
[52] U.S. Cl. ..................................................... 514/182
[58] Field of Search ........................................ 514/182

[56] References Cited

U.S. PATENT DOCUMENTS 4,278,668 7/1981 Guéritée ............................. 514/182

FOREIGN PATENT DOCUMENTS 0066001 12/1982 European Pat. Off. ............ 514/182
8601208 2/1986 World Int. Prop. O. .......... 514/182

*Primary Examiner*—Leonard Schenkman
*Assistant Examiner*—Joseph A. Lipovsky
*Attorney, Agent, or Firm*—Gifford, Groh, Sheridan, Sprinkle and Dolgorukov

[57] ABSTRACT

This invention relates to pharmaceutical compositions endowed with anti-progesteronic properties. This invention provides pharmaceutical compositions containing a pharmacologically effective amount of a 17$\beta$-OR 17$\alpha$-ethynyl-5$\alpha$-androst-2-ene in admixture or conjunction with an innocuous pharmaceutical carrier or vehicle. The pharmaceutical compositions according to this invention are useful to prevent nidation or gestation.

8 Claims, No Drawings

NOVEL PHARMACEUTICAL COMPOSITIONS ENDOWED WITH ANTI-PROGESTERONIC PROPERTIES AND A PROCESS FOR MAKING THE SAME

BACKGROUND OF THE INVENTION

I. Field of the Invention

This invention relates to novel pharmaceutical compositions intended to prevent the effects of natural progesterone.

More precisely it relates to novel pharmaceutical compositions containing as their active ingredient an anti-progesterone effective amount of a Δ-2 androstenic derivative of formula I:

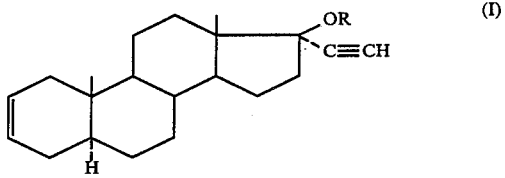

wherein: R is a hydrogen, the acyl residue of an organic carboxylic acid, a lower alkyl radical or the tetrahydropyranyl radical,
in admixture or conjunction with an inert, nontoxic and pharmaceutically acceptable carrier or vehicle.

II. Description of the Prior Art

These compounds and most particularly the 17β-acetoxy derivative have already been disclosed in the literature, specifically in British Pat. No. 1492746. More recently, processes for their purification have been disclosed, for example, in European Pat. No. 66 601, or in European Patent Application No. 86-4006226, filed on Mar. 25, 1986, in the name of Laboratoire Theramex. The known biological properties of these compounds are defined by gonadotropic curbing actions on the hypophysis and the gonads, and are evidenced by the involution of the ovaries and testes in laboratory animals.

Previously disclosed therapeutic uses for the compounds of formula I related to endometriosis, to benign disease of the breast and to pseudogestation in animals, namely in female dogs.

SUMMARY OF THE PRESENT INVENTION

More recent biological studies have shown that these compounds when given orally or by injection under the hereinafter mentioned conditions strongly interfere with the physiological effects of progesterone, acting as an antagonist of this hormone when administered to mammals in a physiologically effective amount.

DETAILED DESCRIPTION OF THE PREFERRED EMBODIMENT OF THE PRESENT INVENTION

Even at high doses (25 mg in rabbits) the compounds of formula I (the main representative of which is 17α-ethynyl-17β-acetoxy-5α-androst-2-ene) induce only a weak pseudogestative action, i.e. <2.5% of that of progesterone. To the contrary, they antagonize the action of progesterone in rabbits after administration either orally or parenterally. Evaluation of the inhibiting action on endometrium proliferation due to progesterone was based on a determination according to Clauberg's test and Mac Phail's index, well-accepted evaluative criteria.

The observed inhibition was statistically significant when the compounds were administered by sub-cutaneous route at single doses of 5 mg, and total doses of 10 mg, against 1.9 mg of injected progesterone.

The action of 17β-acetoxy-17α-ethynyl-5α-androst-2-ene is more significant by oral administration. The observed inhibition was practically total at 5 mg against 0.24 mg of injected progesterone. Inhibition was also very marked at doses of 10 mg against 1.9 mg of injected progesterone.

Given to rats by mouth before nidation (one to five days after mating of gestating rats) at doses of 5 mg/kg/day, the compounds of formula I made gestation impossible. Under the same conditions of treatment they decreased the number of fetuses which implanted, comparison to a dose of 1.25 mg/kg/day in the rat.

In rabbits, gestation was prevented by a dose as low as 5 mg/kg/day, given from the time of mating.

Moreover, 17β-acetoxy-17α-ethynyl-5α-androst-2-ene also showed an anti-nidatory and an abortive action at the same time.

The pharmaceutical compositions according to this invention are hence efficient medicines to impede nidation and gestation in humans when given at the start of the pregnancy. They can be used either orally or parenterally.

The necessary dosages range from 50 to 200 mg/pay administered for several days. The daily administration may be fractionated into several smaller doses.

Another therapeutic use of the compositions according to this invention, as a result of this anti-progestative action, is the voluntary induction of menses in mammals before the end of the luteal phase of a normal cycle.

This anti-progesteronic effect, which induces an anti-progestative action, is surprising since it does not result either from an anti-gonadotropic action, or from a competitive action at the molecular level. The compounds of general formula I do not show any affinity for the specific receptors of progesterone, as is the case with Roussel Uclaf's compound RU 38486 (Mifepristone) (trademark).

The pharmaceutical compositions according to this invention preferably contain from 25 to 250 mg of a compound of formula I per unit dosage.

The pharmaceutical compositions according to this invention are suitable for administration by oral, parenteral, rectal or vaginal route.

For this purpose pharmaceuticals containing these compounds can be administered in the form of tablets, coated tablets, dragees, capsules, lozenges, film-coated tablets, soft gelatin capsules, hard gelatin capsules (with a liquid phase inserted therein), pills, cachets, injectable solutions or suspensions divided in ampuls, auto-injectable syringes, or in multi-dose flasks.

Vehicles or carriers for pharmaceutical administration include water, saline, isotonic aqueous mediums, aqueous solutions containing polyethyleneglycols, and aqueous solutions of polyvinylpyrrolidone (for the injectable preparations); conventional carriers such as starches, cellulose, magnesium carbonate, calcium phosphate, silica, magnesium stearate, and talc; or binders, sweetening agents, flavoring agents, and agents which improve the taste of the solid preparations. The compounds can also be used in forms suitable for rectal administration such as suppositories or rectal capsules.

Carriers for rectal administration include cocoa butter or polyethyleneglycol stearate.

This invention also provides a process for producing pharmaceutical compositions endowed with anti-progesteronic activity which is defined by incorporating an anti-progesteronic amount of a compound of formula I:

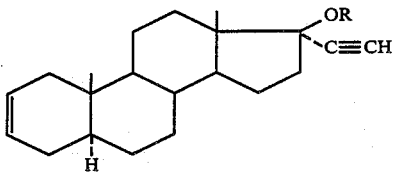

wherein R has the above given definitions, admixed or put in conjunction with an inert, nontoxic and pharmaceutically acceptable carrier or vehicle.

This manufacture or this admixture is performed according to the known methods of pharmacology.

The experimental part which appears hereinafter summarizes the various assays performed in the animals and merely illustrates the invention.

EXAMPLE I

Tablets of 17α-ethynyl-17β-acetoxy-5α-androst-2-ene were prepared in the following proportions:

| | |
|---|---|
| 17α-ethynyl-17β-acetoxy-5α-androst-2-ene | 50 g |
| wheat starch | 47 g |
| corn starch | 61 g |
| microcrystalline cellulose | 12 g |
| cross-linked polyvinylpyrrolidone | 8 g |
| magnesium carbonate | 26 g |
| magnesium stearate | 15 g |
| talc | 6 g | for 1000 tablets finished at a mean weight of 225 g.

EXAMPLE II

An injectable solution of 17α-ethynyl-17β-acetoxy-5α-androst-2-ene was prepared in the following proportions:

| | |
|---|---|
| 17α-ethynyl-17β-acetoxy-5α-androst-2-ene | 10 g |
| benzylic alcohol | 4.5 ml |
| sterile olive oil q. enough for | 200 ml |

This solution was divided in 2 ml ampuls each containing 100 mg of active ingredient.

EXAMPLE III

Progestomimetic and anti-progesteronic activity of the compounds of formula I:

The anti-progesteronic activity of the compounds of formula I was demonstrated using Clauberg's test, modified according to Mac Phail (J. Physiol. (London) 83 (1934) 145). Impubescent female rabbits of a means weight of 1.5 kg were, for 5 consecutive days, given a subcutaneous injection of 5 mg of Estradiol benzoate. After these five days of sensibilisation, the animals were given, from the sixth day and on every day for five days, a subcutaneous injection of the product to be tested, or of progesterone as a comparison.

The rabbits were sacrificed after the last administration. The uteri were excised, fixed in Bouin's solution and then embedded in paraffin. Chips of 5 m thickness were cut out by microtome and were stained using a mixture of Hemalun-Eosin-Saffron. The growth of the endometrial lacy structure observed by microscope was evaluated according to the scale given by Mac Phail.

The compounds of formula I did not cause any endometrial proliferation up to doses of 25 mg for 5 days. The pseudogestative action was less than 25% of that of progesterone.

The anti-progesteronic activity was also shown using a variant of Mac Phail's test. After the preliminary step of sensibilization using Estradiol benzoate, the animals were subcutaneously given an active amount of progesterone for five days. A compound of formula I was given at the same time, either subcutaneously or orally. 24 hours after the last administration the animals were sacrificed and the uteri analysed from a histological point of view. The endometrial proliferation was determined according to Mac Phail's Index.

Results (a) After oral administration of a compound of formula I:

| Compound | Dose in mg/animal and per day | Number of animals | Quotation according to Mac Phail's Index |
|---|---|---|---|
| Progesterone | 0.24 mg | 7 | 2.9 ± 0.2 |
| Progesterone | 0.24 mg + compound of formula I 5 mg | 4 | 2.1 ± 0.7 (0.05 ≧ p ≧ 0.01) |
| | 10 mg | 4 | 0.6 ± 0.1 (p ≦ 0.001) |
| | 20 mg | 4 | 0.8 ± 0.4 (p ≦ 0.001) |
| | 40 mg | 4 | 0.1 ± 0.1 (p ≦ 0.001) |
| Progesterone | 1.92 mg | 6 | 3.3 ± 0.1 |
| Progesterone | 1.92 mg + compound of formula I 5 mg | 4 | 3.3 ± 0.1 (NS) |
| | 10 mg | 3 | 3.0 ± 0.5 (NS) |
| | 20 mg | 4 | 0.8 ± 0.1 (p ≦ 0.001) |
| | 40 mg | 4 | 0.9 ± 0.9 (p ≦ 0.001) |

(b) After subcutaneous injection of a compound of formula I:

| Compound | Dose in mg/animal and per day | Number of animals | Quotation according to MAC Phail's Index |
|---|---|---|---|
| Progesterone | 0.24 mg | 7 | 2.9 ± 0.2 |

-continued

| Compound | Dose in mg/animal and per day | Number of animals | Quotation according to MAC Phail's Index |
|---|---|---|---|
| Progesterone | 0.24 mg + compound of formula I 5 mg | 4 | 2.1 ± 0.7 (0.05 ≧ p ≧ 0.01) |
| | 10 mg | 4 | 0.6 ± 0.1 (p ≦ 0.001) |
| | 20 mg | 4 | 0.8 ± 0.4 (p ≦ 0.001) |
| | 40 mg | 4 | 0.1 ± 0.1 (p ≦ 0.001) |
| Progesterone | 1.92 mg | 6 | 3.3 ± 0.1 |
| Progesterone | 1.92 mg + compound of formula I 5 mg | 4 | 3.3 ± 0.1 NS |
| | 10 mg | 3 | 3.0 ± 0.5 NS |
| | 20 mg | 4 | 0.8 ± 0.1 (p ≦ 0.001) |
| | 40 mg | 4 | 0.9 ± 0.4 (p ≦ 0.001) |

The compounds of formula I, which were practically devoid of any progesteromimetic activity, show antiprogesteronic activity mainly by oral administration. This activity was observed to be dose-dependent and proportional to the administered dose.

The activity achieved by subcutaneous administration appeared to be somewhat less clear.

What is claimed is:

1. A method of inducing menses, impairing nidation, or inducing abortion in a mammal comprising the step of reducing endometrial proliferation in said mammal by administering to said mammal at an appropriate time in its menstrual cycle a pharmaceutically effective amount of 17β-OR-17α-ethynyl-5α-androst-2-ene, wherein R is hydrogen, an acyl residue of an organic carboxylic acid having from one to ten carbon atoms, a lower alkyl radical having from one to ten carbon atoms, or a tetrahydropyranyl radical.

2. The method according to claim 1, wherein said administration is carried out by parenteral, oral, rectal or vaginal route.

3. The method according to claim 1, further comprising admixing or conjoining said androst-2-ene with a suitable carrier or diluent prior to said administration.

4. The method according to claim 3, wherein said carrier or diluent is water, saline solution, an isotonic aqueous medium, an aqueous solution containing a polyethlene glycol, starch, cellulose, magnesium carbonate, calcium phosphate, silica, magnesium stearate, or talc.

5. The method according to claim 3, wherein said admixing or conjoining step comprises configuring said androst-2-ene and said carrier or diluent as a tablet, a coated tablet, a dragee, a capsule, a lozenge, a film-coated tablet, a soft gelatin capsule, a hard gelatin capsule having a liquid phase therein, a pill, a cachet, an injectable solution, or an injectable suspension.

6. The method according to claim 1, wherein said administration is carried out in a unit dosage range of about 10 to 250 mg.

7. The method according to claim 1, wherein administration is carried out by parenteral route, and said method further comprises admixing or conjoining said androst-2-ene with a suitable carrier or diluent in a unit dosage range of about 25 to 100 mg.

8. The method according to claim 1, wherein said administration is carried out by oral route, and said method further comprises admixing or conjoining said androst-2-ene with a suitable carrier or diluent in a unit dosage range of about 50 to 100 mg.

* * * * *